United States Patent
Tsutaoka

(10) Patent No.: US 11,823,382 B2
(45) Date of Patent: *Nov. 21, 2023

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Takuya Tsutaoka, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 476 days.

This patent is subject to a terminal disclaimer.

(21) Appl. No.: 17/223,169

(22) Filed: Apr. 6, 2021

(65) Prior Publication Data

US 2021/0219941 A1 Jul. 22, 2021

Related U.S. Application Data

(63) Continuation of application No. PCT/JP2019/039050, filed on Oct. 3, 2019.

(30) Foreign Application Priority Data

Oct. 12, 2018 (JP) .................................. 2018-193253

(51) Int. Cl.
A61B 8/00 (2006.01)
A61B 8/08 (2006.01)
(Continued)

(52) U.S. Cl.
CPC .............. *G06T 7/0012* (2013.01); *A61B 8/08* (2013.01); *A61B 8/461* (2013.01); *A61B 8/54* (2013.01);
(Continued)

(58) Field of Classification Search
CPC ........... G06T 7/0012; G06T 7/50; G06T 7/73; G06T 2207/10132; G06T 2207/30081;
(Continued)

(56) References Cited

U.S. PATENT DOCUMENTS 8,788,019 B2 * 7/2014 Downey .............. A61B 8/4461
600/437
8,926,513 B2 * 1/2015 Yao ...................... A61B 8/5223
600/443
(Continued)

FOREIGN PATENT DOCUMENTS

JP 2001-218768 A 8/2001
JP 2005-534462 A 11/2005
(Continued)

OTHER PUBLICATIONS

McGahan John P. et al.; Ultrasound probe pressure as a source of error in prostate localization for external beam radiotherapy; International Journal of Radiation: Oncology Biology Physics; Pergamon press, USA.; Nov. 1, 2004; pp. 788-793; vol. 60; No. 3; XP004600528.
(Continued)

*Primary Examiner* — Gregory M Desire
(74) *Attorney, Agent, or Firm* — Studebaker & Brackett PC

(57) ABSTRACT

An ultrasound diagnostic apparatus 1 includes an image acquisition unit 17 that acquires an ultrasound image of a subject a bladder extraction unit 18 that extracts a bladder from the ultrasound image; a prostate extraction unit 19 that extracts a prostate or cervix from the ultrasound image from which the bladder is extracted; a region-of-interest setting unit 20 that sets a region of interest at a depth position in the ultrasound image based on a position of the extracted prostate or cervix in a case where the prostate or cervix is extracted and that sets a region of interest at a depth position in the ultrasound image based on a position of the extracted bladder in a case where the prostate or cervix is not extracted; and an image quality adjustment unit 21 that adjusts the transmission/reception condition according to the depth position of the region of interest.

21 Claims, 6 Drawing Sheets

(51) Int. Cl.
| | |
|---|---|
| *G06K 9/46* | (2006.01) |
| *G06T 7/00* | (2017.01) |
| *G06T 7/50* | (2017.01) |
| *G06T 7/73* | (2017.01) |
| *G01S 15/89* | (2006.01) |

(52) U.S. Cl.
CPC ...... *G01S 15/8977* (2013.01); *G01S 15/8993* (2013.01); *G06T 7/50* (2017.01); *G06T 7/73* (2017.01); *A61B 8/4488* (2013.01); *G06T 2207/10132* (2013.01); *G06T 2207/30081* (2013.01)

(58) Field of Classification Search
CPC .. A61B 8/08; A61B 8/461; A61B 8/54; A61B 8/4488; G01S 15/8977; G01S 15/8993
See application file for complete search history.

(56) References Cited

U.S. PATENT DOCUMENTS

| | | | |
|---|---|---|---|
| 10,368,841 B2* | 8/2019 | Fujiwara | G16H 50/30 |
| 11,071,523 B2* | 7/2021 | Miyake | G16H 50/30 |
| 11,399,801 B2* | 8/2022 | Murakami | A61B 8/12 |
| 2001/0016686 A1 | 8/2001 | Okada et al. | |
| 2004/0024315 A1 | 2/2004 | Chalana et al. | |
| 2004/0081340 A1* | 4/2004 | Hashimoto | A61B 8/463 382/128 |
| 2009/0123047 A1 | 5/2009 | Yfantis | |
| 2015/0018666 A1* | 1/2015 | Madabhushi | A61B 10/0233 600/411 |
| 2018/0064413 A1 | 3/2018 | Nakanishi et al. | |
| 2018/0146956 A1 | 5/2018 | Imai | |
| 2018/0303460 A1 | 10/2018 | Shin et al. | |
| 2020/0383658 A1 | 12/2020 | Wang et al. | |
| 2021/0330285 A1* | 10/2021 | Lu | G16H 30/20 |

FOREIGN PATENT DOCUMENTS

| | | |
|---|---|---|
| JP | 2016-195748 A | 11/2016 |
| WO | 2017/069451 A1 | 4/2017 |
| WO | 2018/129737 A1 | 7/2018 |

OTHER PUBLICATIONS

Murad-Regadas S. M. et al.; "Dynamic translabial ultrasound versus echodefecography combined with the endovaginal approach to assess pelvic floor dysfunctions: How effective are these techniques?"; Techniques in Coloproctology; vol. 21; No. 7; Jul. 3, 2017; pp. 555-565; XP036295915; Springer.

Michael Pinkawa et al.; "Image-Guided Radiotherapy for Prostate Cancer; Implementation of ultrasound—based prostate localization for the analysis of inter - and intrafraction organ motion"; Strahlentherapie und Onkologie; Dec. 24, 2008; pp. 679-685; vol. 184; No. 12; XP019660163; Urban & Vogel.

The extended European search report issued by the European Patent Office dated Nov. 11, 2021, which corresponds to European Patent Application No. 19870617.8-1126 and is related to U.S. Appl. No. 17/223,169.

International Search Report issued in PCT/JP2019/039050; dated Dec. 10, 2019.

International Preliminary Report on Patentability and Written Opinion issued in PCT/JP2019/039050; dated Apr. 8, 2021.

Sato, Takahiro et al.: Diagnosis of rectal varices with color Doppler ultrasonography, Japanese Journal of Portal Hypertension, 2011, 17, pp. 109-113.

Karasawa, Kenichi et al.: Automated organ localization based on anatomical landmark and its application to multi-atlas pancreas segmentation, Ihich Technical Report, vol. 115, No. 401, Jan. 12, 2016, pp. 215-220.

Csurka et al.: Visual Categorization with Bags of Keypoints, Proc. of ECCV Workshop on Statistical Learning in Computer Vision, pp. 59-74 (2004).

Krizhevsk et al.: ImageNet Classification with Deep Convolutional Neural Networks, Advances in Neural Information Processing Systems 25, pp. 1106-1114 (2012).

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2019/039050 filed on Oct. 3, 2019, which claims priority under 35 U.S.C § 119(a) to Japanese Patent Application No. 2018-193253 filed on Oct. 12, 2018. Each of the above application(s) is hereby expressly incorporated by reference, in its entirety, into the present application.

BACKGROUND OF THE INVENTION

1. Field of the Invention

The present invention relates to an ultrasound diagnostic apparatus and a control method of an ultrasound diagnostic apparatus, and more particularly, to an ultrasound diagnostic apparatus and a control method of an ultrasound diagnostic apparatus which are used to evaluate the rectal stool of a subject.

2. Description of the Related Art

Hitherto, in a medical field, an ultrasound diagnostic apparatus using an ultrasound image has been put to practical use. Generally, this kind of ultrasound diagnostic apparatus includes an ultrasound probe having a built-in transducer array and an apparatus body connected to the ultrasound probe, in which ultrasonic waves are transmitted from the ultrasound probe toward a subject, the ultrasound probe receives ultrasound echoes from the subject, and the apparatus body electrically processes the received signal to generate an ultrasound image.

The condition of rectal stool of the subject has been evaluated by examining the rectum of the subject by using such an ultrasound diagnostic apparatus. For example, JP2016-195748A discloses an ultrasound diagnostic apparatus that analyzes the ultrasound echoes from the large intestine of the subject, thereby automatically evaluating the condition of stool inside the large intestine.

SUMMARY OF THE INVENTION

Incidentally, upon the examination of the lower abdomen of the subject using the ultrasound diagnostic apparatus, it is desirable for the user to examine the subject within a limited time in order to reduce the burden on the subject. Further, in recent years, a portable ultrasound diagnostic apparatus has been developed, and the examination of the lower abdomen of the subject using the ultrasound diagnostic apparatus has been performed even in a field of home medical care. In particular, in such a field of home medical care, there are many users who are unfamiliar with the examination of the rectum using the ultrasound diagnostic apparatus. The user needs to perform the examination of the subject without omission within a limited time, and thus it has been required to reduce manually setting and operating the ultrasound diagnostic apparatus so that a low-skilled user also easily performs the ultrasonic examination.

However, in general, since the transmission/reception conditions of the ultrasonic waves suitable for depicting the rectum of the subject vary greatly depending on individual differences between the subjects, the health condition of the subject, the time of examination, and the like, the user needs to manually set the transmission/reception conditions of the ultrasonic waves every time the examination of the rectum of the subject is started, which causes a problem that a lot of effort and time are required upon the examination. In particular, in a case where the low-skilled user examines the rectum by using the ultrasound diagnostic apparatus, more effort and time may be required.

The present invention has been made to solve such a conventional problem and an object thereof is to provide an ultrasound diagnostic apparatus and a control method of an ultrasound diagnostic apparatus which can reduce the effort of the user and can easily perform examination regardless of the skill level of the user.

In order to achieve the above object, a first ultrasound diagnostic apparatus according to an aspect of the present invention comprises an ultrasound probe; an image acquisition unit that acquires an ultrasound image of a subject by performing transmission and reception of an ultrasound beam to and from the ultrasound probe in accordance with a predetermined transmission/reception condition; a display unit that displays the ultrasound image acquired by the image acquisition unit; a bladder extraction unit that extracts a bladder based on the ultrasound image acquired by the image acquisition unit; a prostate extraction unit that extracts a prostate based on the ultrasound image from which the bladder is extracted by the bladder extraction unit; a region-of-interest setting unit that sets a region of interest at a depth position in the ultrasound image based on a position of the extracted prostate in a case where the prostate is extracted by the prostate extraction unit and that sets a region of interest at a depth position in the ultrasound image based on a position of the bladder extracted by the bladder extraction unit in a case where the prostate is not extracted by the prostate extraction unit; and an image quality adjustment unit that adjusts the transmission/reception condition according to the depth position of the region of interest set by the region-of-interest setting unit.

In this case, in a case where the prostate is extracted by the prostate extraction unit, the region-of-interest setting unit may set the region of interest at a position deeper than the position of the extracted prostate by a predetermined first distance.

Alternatively, in a case where the prostate is not extracted by the prostate extraction unit, the region-of-interest setting unit may set the region of interest at a position deeper than the position of the bladder extracted by the bladder extraction unit by a second distance longer than the first distance.

In addition, a second ultrasound diagnostic apparatus according to another aspect of the present invention comprises an ultrasound probe; an image acquisition unit that acquires an ultrasound image of a subject by performing transmission and reception of an ultrasound beam to and from the ultrasound probe in accordance with a predetermined transmission/reception condition; a display unit that displays the ultrasound image acquired by the image acquisition unit; a bladder extraction unit that extracts a bladder based on the ultrasound image acquired by the image acquisition unit; a cervix extraction unit that extracts a cervix based on the ultrasound image from which the bladder is extracted by the bladder extraction unit; a region-of-interest setting unit that sets a region of interest at a depth position in the ultrasound image based on a position of the extracted cervix in a case where the cervix is extracted by the cervix extraction unit and that sets a region of interest at a depth position in the ultrasound image based on a position of the bladder extracted by the bladder extraction unit in a case where the cervix is not extracted by the cervix extraction unit; and an image quality adjustment unit that adjusts the transmission/reception condition according to the depth position of the region of interest set by the region-of-interest setting unit.

In this case, in a case where the cervix is extracted by the cervix extraction unit, the region-of-interest setting unit may set the region of interest at a position deeper than the position of the extracted cervix by a predetermined first distance.

Alternatively, in a case where the cervix is not extracted by the cervix extraction unit, the region-of-interest setting unit may set the region of interest at a position deeper than the position of the bladder extracted by the bladder extraction unit by a second distance longer than the first distance.

Further, the region-of-interest setting unit may set the region of interest having a width corresponding to a width of the bladder at a lateral position corresponding to the position of the bladder extracted by the bladder extraction unit.

Alternatively, the region-of-interest setting unit may set the region of interest over an entire ultrasound image in a lateral direction at the depth position of the region of interest.

The image quality adjustment unit may adjust a gain of the ultrasound image according to an image quality of the ultrasound image in the region of interest.

Alternatively, the image quality adjustment unit may adjust a dynamic range of the ultrasound image according to an image quality of the ultrasound image in the region of interest.

In addition, it is preferable that the ultrasound diagnostic apparatus further comprises a rectal stool evaluation unit that evaluates rectal stool, based on the ultrasound image acquired by the image acquisition unit in accordance with the transmission/reception condition adjusted by the image quality adjustment unit.

A control method of an ultrasound diagnostic apparatus according to a still another aspect of the present invention comprises acquiring an ultrasound image of a subject by performing transmission and reception of an ultrasound beam to and from the ultrasound probe in accordance with a predetermined transmission/reception condition; displaying the acquired ultrasound image; extracting a bladder based on the acquired ultrasound image; extracting a prostate or cervix based on the ultrasound image from which the bladder is extracted; setting a region of interest at a depth position in the ultrasound image based on a position of the extracted prostate or cervix in a case where the prostate or cervix is extracted and setting a region of interest at a depth position in the ultrasound image based on a position of the extracted bladder in a case where the prostate or cervix is not extracted; and adjusting the transmission/reception condition according to the depth position of the set region of interest.

According to the present invention, the ultrasound diagnostic apparatus comprises a bladder extraction unit that extracts a bladder based on the ultrasound image acquired by the image acquisition unit; a prostate extraction unit that extracts a prostate or a cervix extraction unit that extracts a cervix, based on the ultrasound image from which the bladder is extracted by the bladder extraction unit; a region-of-interest setting unit that sets a region of interest at a depth position in the ultrasound image based on a position of the extracted prostate or cervix in a case where the prostate is extracted by the prostate extraction unit or the cervix is extracted by the cervix extraction unit and that sets a region of interest at a depth position in the ultrasound image based on a position of the bladder extracted by the bladder extraction unit in a case where the prostate is not extracted by the prostate extraction unit or the cervix is not extracted by the cervix extraction unit; and an image quality adjustment unit that adjusts the transmission/reception condition according to the depth position of the region of interest set by the region-of-interest setting unit. Therefore, the effort of the user can be reduced and the examination can be easily performed regardless of the skill level of the user.

DESCRIPTION OF THE PREFERRED EMBODIMENTS

Hereinafter, embodiments of the present invention will be described with reference to the accompanying drawings.

First Embodiment

Figure 1:
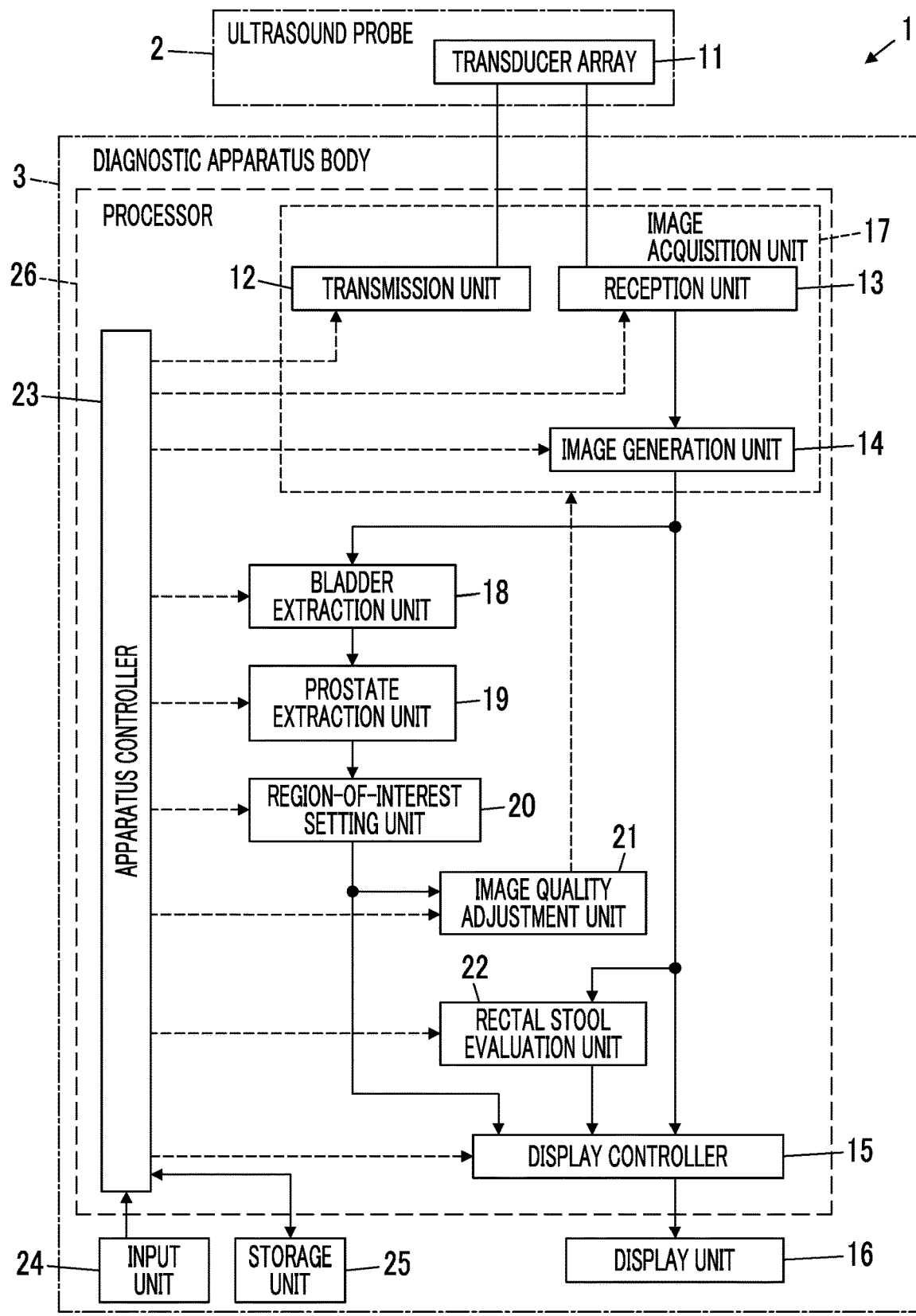
FIG. 1 is a block diagram showing a configuration of an ultrasound diagnostic apparatus according to a first embodiment of the present invention.

FIG. 1 shows the configuration of an ultrasound diagnostic apparatus 1. As shown in FIG. 1, the ultrasound diagnostic apparatus 1 has an ultrasound probe 2 and a diagnostic apparatus body 3, and the ultrasound probe 2 and the diagnostic apparatus body 3 are connected to each other. The ultrasound probe 2 comprises a transducer array 11. Here, the ultrasound probe 2 and the diagnostic apparatus body 3 may be connected wiredly or wirelessly to each other.

The diagnostic apparatus body 3 comprises a transmission unit 12 and a reception unit 13, and the transmission unit 12 and the reception unit 13 are connected to the transducer array 11 of the ultrasound probe 2. Further, the reception unit 13 is sequentially connected to the image generation unit 14, the display controller 15, and the display unit 16. Here, the transmission unit 12, the reception unit 13, and the image generation unit 14 constitute an image acquisition unit 17. In addition, a bladder extraction unit 18 is connected to the image generation unit 14, and a prostate extraction unit 19, a region-of-interest setting unit 20, and the display controller 15 are sequentially connected to the bladder extraction unit 18. Further, an image quality adjustment unit 21 is connected to the region-of-interest setting unit 20. Furthermore, a rectal stool evaluation unit 22 is connected to the image generation unit 14, and the display controller 15 is connected to the rectal stool evaluation unit 22.

Further, an apparatus controller 23 is connected to the transmission unit 12, the reception unit 13, the image generation unit 14, the display controller 15, the bladder extraction unit 18, the prostate extraction unit 19, the region-of-interest setting unit 20, the image quality adjustment unit 21, and the rectal stool evaluation unit 22. An input unit 24 and a storage unit 25 are connected to the apparatus controller 23. Here, the apparatus controller 23 and the storage unit 25 are connected to each other such that information can be exchanged in both directions.

Furthermore, the display controller 15, the image acquisition unit 17, the bladder extraction unit 18, the prostate extraction unit 19, the region-of-interest setting unit 20, the image quality adjustment unit 21, the rectal stool evaluation unit 22, and the apparatus controller 23 constitute a processor 26.

The transducer array 11 of the ultrasound probe 2 shown in FIG. 1 has a plurality of transducers arranged one-dimensionally or two-dimensionally. Each of the transducers transmits ultrasonic waves in accordance with a drive signal supplied from the transmission unit 12, receives ultrasound echoes from the subject, and outputs the received signal. For example, each transducer is formed by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 12 of the image acquisition unit 17 includes, for example, a plurality of pulse generators, and the transmission unit 12 adjusts the amount of delay of each drive signal based on a transmission delay pattern selected according to a control signal from the apparatus controller 23 in accordance with the preset transmission condition of the ultrasonic waves, and supplies the drive signals to the plurality of transducers so that the ultrasonic waves transmitted from the plurality of transducers of the transducer array 11 form an ultrasound beam. In this manner, in a case where a pulsed or continuous-wave voltage is applied to the electrodes of the plurality of transducers of the transducer array 11, the piezoelectric body expands and contracts to generate pulsed or continuous-wave ultrasonic waves from each transducer. From the combined wave of these ultrasonic waves, the ultrasound beam is formed.

The transmitted ultrasound beam is reflected by a target, for example, a site of the subject, and propagates toward the transducer array 11 of the ultrasound probe 2. The ultrasound echoes propagating toward the transducer array 11 in this manner are received by each transducer constituting the transducer array 11. In this case, each transducer constituting the transducer array 11 expands and contracts by receiving the propagating ultrasound echoes to generate an electrical signal, and outputs the electrical signal to the reception unit 13.

The reception unit 13 of the image acquisition unit 17 processes the received signal output from the transducer array 11, based on the control signal from the apparatus controller 23 in accordance with the reception condition of the preset ultrasonic waves.

Figure 2:
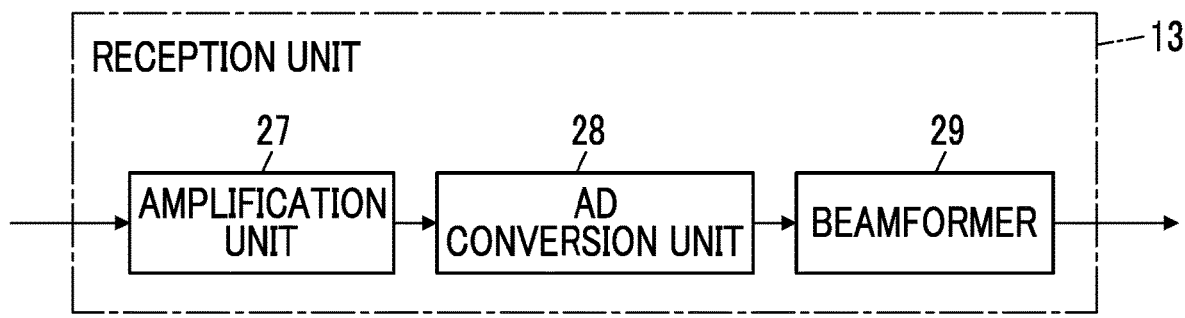
FIG. 2 is a block diagram showing an internal configuration of a reception unit according to the first embodiment of the present invention.

As shown in FIG. 2, the reception unit 13 has a configuration in which an amplification unit 27, an analog digital (AD) conversion unit 28, and a beamformer 29 are connected to one another in series. The amplification unit 27 amplifies the received signal received from each transducer constituting the transducer array 11, and transmits the amplified received signal to the AD conversion unit 28. The AD conversion unit 28 converts the received signal transmitted from the amplification unit 27 into digital data, and sends the data to the beamformer 29. In this case, the AD conversion unit 28 sets a dynamic range of the digital data to a predetermined value. Based on a reception delay pattern selected according to the control signal from the apparatus controller 23, the beamformer 29 performs reception focusing processing in which addition (phasing addition) is performed by giving delays to respective pieces of data according to a set sound speed. Through the reception focusing processing, a sound ray signal in which the focus of the ultrasound echo is narrowed on a fixed scanning line is generated. The sound ray signal generated in this manner is sent to the image generation unit 14.

Figure 3:
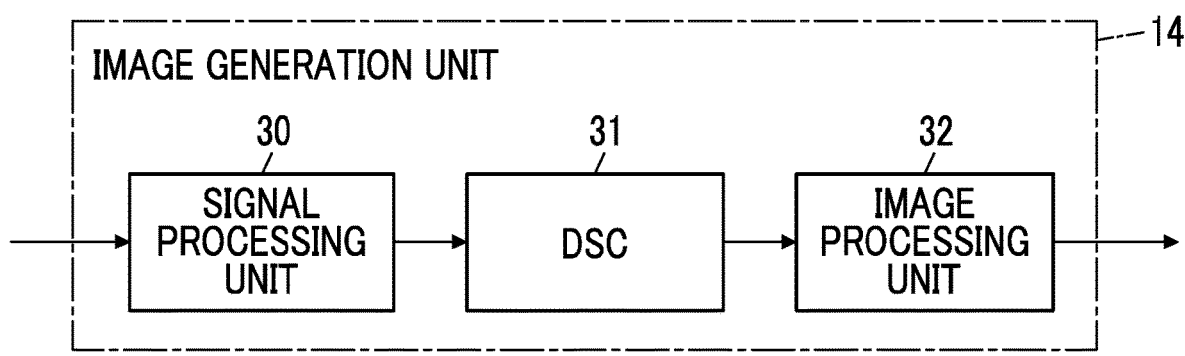
FIG. 3 is a block diagram showing an internal configuration of an image generation unit according to the first embodiment of the present invention.

As shown in FIG. 3, the image generation unit 14 of the image acquisition unit 17 has a configuration in which a signal processing unit 30, a digital scan converter (DSC) 31, and an image processing unit 32 are connected to one another in series. The signal processing unit 30 corrects the attenuation of the generated sound ray signal, which is caused by the propagation distance according to the depth of the reflection position of the ultrasonic wave, and then performs envelope detection processing to generate a B-mode image signal representing a tissue in a subject. The B-mode image signal generated in this manner is output to the DSC 31.

The DSC 31 of the image generation unit 14 raster-converts the B-mode image signal into an image signal according to a normal television signal scanning method to generate an ultrasound image. The image processing unit 32 of the image generation unit 14 performs various kinds of necessary image processing such as brightness correction, gradation correction, sharpness correction, and color correction on the image data obtained by the DSC 31, and then outputs the ultrasound image to the display controller 15, the bladder extraction unit 18, and the rectal stool evaluation unit 22.

The bladder extraction unit 18 of the processor 26 extracts a bladder based on the ultrasound image acquired by the image acquisition unit 17. In a case of extracting the bladder from the ultrasound image, the bladder extraction unit 18 stores, for example, typical pattern data in advance as a template, calculates the similarity to the pattern data while searching the image with the template, and thereby can extract the bladder on the assumption that the bladder is present at the place where the similarity is equal to or more than a threshold value, or maximum.

In addition to the simple template matching, in order to calculate the similarity, for example, a machine learning method described in Csurka et al.: Visual Categorization with Bags of Keypoints, Proc. of ECCV Workshop on Statistical Learning in Computer Vision, pp. 59 to 74 (2004), a general image recognition method using deep learning described in Krizhevsk et al.: ImageNet Classification with Deep Convolutional Neural Networks, Advances in Neural Information Processing Systems 25, pp. 1106 to 1114 (2012) may be used.

The prostate extraction unit 19 of the processor 26 extracts the prostate based on the ultrasound image from which the bladder is extracted by the bladder extraction unit 18. In this case, the prostate extraction unit 19 may extract the prostate in the ultrasound image by using, for example, a template matching, a machine learning method, a general image recognition method using deep learning, in the same manner as the bladder extraction unit 18.

The region-of-interest setting unit 20 of the processor 26 sets a region of interest at a depth position in the ultrasound image in which the rectum is assumed to be present, based on the position of the bladder extracted by the bladder extraction unit 18 or the position of the prostate extracted by the prostate extraction unit 19. More specifically, the region-of-interest setting unit 20 sets a region of interest at a position deeper than the position of the extracted prostate by a predetermined first distance D1 in a case where the prostate is extracted by the prostate extraction unit 19, and the region-of-interest setting unit 20 sets a region of interest at a position deeper than the position of the bladder extracted by the bladder extraction unit 18 by a predetermined second distance D2 longer than the first distance D1 in a case where the prostate is not extracted by the prostate extraction unit 19.

The image quality adjustment unit 21 of the processor 26 adjusts the transmission/reception conditions of the ultrasonic waves according to the depth position of the region of interest set by the region-of-interest setting unit 20 such that the inside of the region of interest is clearly depicted. Here, examples of the transmission/reception conditions of the ultrasonic waves include a transmission focus position and a reception focus position of the ultrasonic waves, a display depth of the ultrasound image, and conditions of a gain and a dynamic range of the signal in the reception unit 13 or the image generation unit 14.

Further, in a case where the image quality adjustment unit 21 adjusts the conditions related to the brightness of the ultrasound image by adjusting the condition of the gain, the condition of the dynamic range, or the like, the image quality adjustment unit 21 detects the image quality of the ultrasound image in the region of interest and then adjusts the condition of the gain, the condition of the dynamic range, or the like according to the detected image quality. In this case, the image quality adjustment unit 21 acquires information regarding the brightness of the region of interest such as a median value and a variance value of brightness of the region of interest from the ultrasound image, as information representing the image quality of the ultrasound image in the region of interest.

The rectal stool evaluation unit 22 of the processor 26 evaluates rectal stool, based on the ultrasound image acquired by the image acquisition unit 17 in accordance with the transmission/reception condition of the ultrasonic wave adjusted by the image quality adjustment unit 21. Specifically, the rectal stool evaluation unit 22 performs image analysis on the ultrasound image to evaluate, for example, whether the stool present in the rectum of the subject is loose stool or hard stool.

Under the control of the apparatus controller 23, the display controller 15 of the processor 26 performs predetermined processing on the ultrasound image acquired by the image acquisition unit 17, and causes the display unit 16 to display the ultrasound image.

The display unit 16 of the diagnostic apparatus body 3 displays an image under the control of the display controller 15, and examples thereof include a display device such as a liquid crystal display (LCD) and an organic electroluminescence display (organic EL display).

The apparatus controller 23 of the processor 26 controls each unit of the diagnostic apparatus body 3 based on the program stored in advance in the storage unit 25 or the like and the user's operation through the input unit 24.

The input unit 24 of the diagnostic apparatus body 3 is used for the user to perform an input operation, and may include a keyboard, a mouse, a trackball, a touch pad, a touch panel, and the like.

The storage unit 25 of the diagnostic apparatus body 3 stores the operation program of the diagnostic apparatus body 3 and the like, and as the storage unit 25, for example, recording media such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or a server may be used.

Here, in the diagnostic apparatus body 3, the processor 26 having the display controller 15, the image acquisition unit 17, the bladder extraction unit 18, the prostate extraction unit 19, the region-of-interest setting unit 20, the image quality adjustment unit 21, the rectal stool evaluation unit 22, and the apparatus controller 23 may be configured by a central processing unit (CPU) and a control program for causing the CPU to execute various kinds of processing, by using a field programmable gate array (FPGA), a digital signal processor (DSP), an application specific integrated circuit (ASIC), or other integrated circuits (IC), or by combination thereof.

Alternatively, the display controller 15, the image acquisition unit 17, the bladder extraction unit 18, the prostate extraction unit 19, the region-of-interest setting unit 20, the image quality adjustment unit 21, the rectal stool evaluation unit 22, and the apparatus controller 23 of the processor 26 may be configured by being integrated partially or entirely into one CPU.

Figure 4:
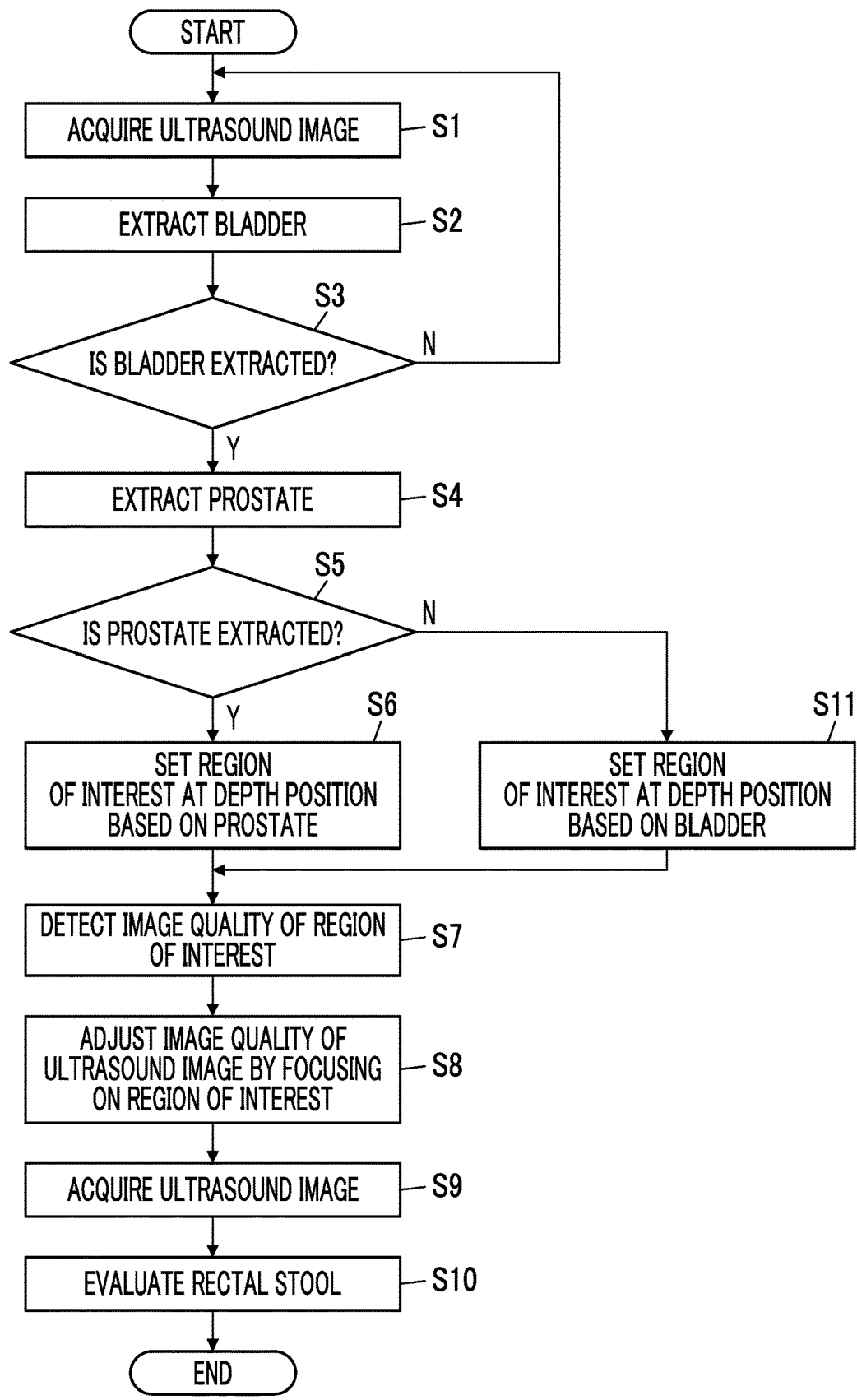
FIG. 4 is a flowchart showing an operation of the ultrasound diagnostic apparatus according to the first embodiment of the present invention.

Next, the operation of the ultrasound diagnostic apparatus 1 according to the first embodiment of the present invention will be described with reference to the flowchart shown in FIG. 4.

First, in Step S1, in order to depict a bladder of a subject, in a state in which the ultrasound probe 2 is in contact with the lower abdomen of the subject by the user's operation, the ultrasound beam is transmitted from the transducer array 11 toward the inside of the subject, and the ultrasound echo from the subject is received by the transducer array 11. Thereby, in a case where the received signal is output from the transducer array 11 to the image acquisition unit 17, the image acquisition unit 17 generates an ultrasound image representing a tomographic image of the lower abdomen of the subject. Here, it is assumed that general-purpose conditions are set as the transmission/reception conditions of the ultrasonic waves in the image acquisition unit 17. Generally, the range of the transmission/reception conditions of ultrasonic waves for depicting the bladder of the subject is wide, and thus the bladder of the subject is easily depicted even in a case where the general-purpose transmission/reception conditions are set.

Next, in Step S2, the bladder extraction unit 18 performs image analysis on the ultrasound image acquired in Step S1, and thereby performs processing of extracting the bladder from the ultrasound image.

In Step S3, determination is made whether or not the bladder is extracted in Step S2. In a case where determination is made that the bladder is not extracted in Step S2, the process returns to Step S1 and then an ultrasound image is newly acquired. In Step S2, the processing of extracting the bladder from the new ultrasound image is performed, and then the process proceeds to Step S3. In this manner, Steps S1 to S3 are repeated until determination is made in Step S3 that the bladder is extracted. In this case, the user moves the position of the ultrasound probe 2 as necessary such that the bladder of the subject is depicted on the ultrasound image. Thereby, in a case where the bladder of the subject is depicted on the ultrasound image and determination is made in Step S3 that the bladder is extracted, the process proceeds to Step S4.

In subsequent Step S4, the prostate extraction unit 19 performs processing of extracting the prostate based on the ultrasound image from which the bladder is extracted in Step S2.

In Step S5, determination is made whether or not the prostate is extracted from the ultrasound image in Step S4. In Step S5, in a case where determination is made that the prostate is extracted, the process proceeds to Step S6.

Figure 5:
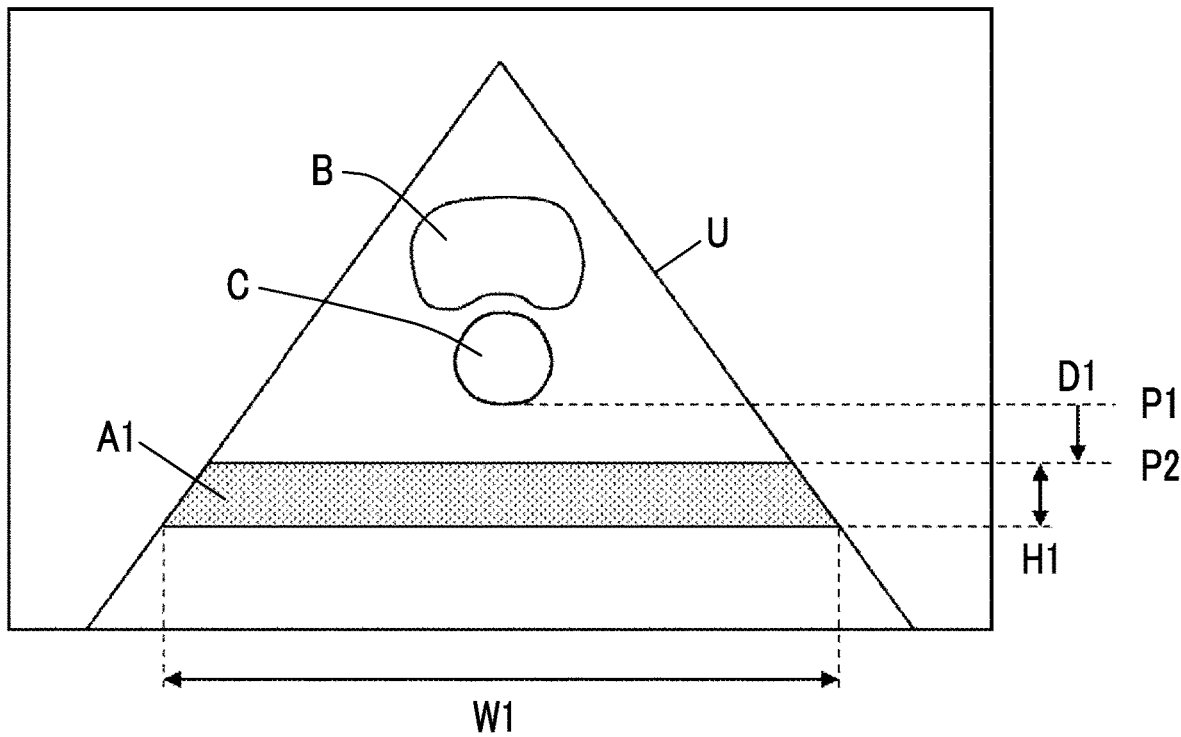
FIG. 5 is a diagram showing a first example of a region of interest according to the first embodiment of the present invention.

In Step S6, the region-of-interest setting unit 20 sets a region of interest in which the rectum is assumed to be present, based on the position of the prostate extracted in Step S4. For example, in a case where determination is made that the prostate is extracted in Step S5, as shown in FIG. 5, the region-of-interest setting unit 20 sets a region of interest A1 at a depth position P2 away from the position P1 of the prostate C in a depth direction by a predetermined first distance D1. In FIG. 5, the upper end of the region of interest A1 is positioned at a depth position P2 away from the position P1 of the lower end of the prostate C in the depth direction by the first distance D1. In addition, the region of interest A1 has a trapezoidal shape set over the entire ultrasound image U in the lateral direction, and has a width W1 in the lateral direction. Further, the region of interest A1 has a height H1 in the depth direction. The height H1 of the region of interest A1 is set to have a width of the typical rectum in the depth direction.

In Step S7, the image quality adjustment unit 21 detects the image quality of the ultrasound image U in the region of interest A1. For example, the image quality adjustment unit 21 acquires information regarding a median value of brightness, a variance value of brightness, or the like in the region of interest A1, and thereby can detect the image quality in the region of interest A1.

In subsequent Step S8, the image quality adjustment unit 21 automatically adjusts the transmission/reception conditions of the ultrasonic waves based on the detection result of the image quality in the region of interest A1 in Step S7, and adjusts the image quality of the ultrasound image U to be generated by the image acquisition unit 17 such that the inside of the region of interest A1 is clearly depicted. In this case, the image quality adjustment unit 21, for example, sets a so-called transmission focus position in the region of interest A1 by adjusting the amount of delay of the drive signal in the transmission unit 12, sets a so-called reception focus position in the region of interest A1 by adjusting the amount of delay of the phasing addition in the beamformer 29 of the reception unit 13, performs setting such that the display depth of the ultrasound image U includes the region of interest A1, and adjusts the gain and the dynamic range in the reception unit 13 or the image generation unit 14. In this manner, since the image quality adjustment unit 21 automatically adjusts the image quality in the region of interest A1, in order to clearly depict the inside of the region of interest A1, the efforts by which the user manually adjusts the transmission/reception conditions of the ultrasonic waves can be omitted.

When the transmission/reception conditions of the ultrasonic waves are adjusted in Step S8, the image acquisition unit 17 newly acquires an ultrasound image U in Step S9. In the ultrasound image U newly acquired in Step S9, the image quality adjustment focusing on the region of interest A1 is performed by the image quality adjustment unit 21, so that the rectum which is assumed to be present in the region of interest A1 is clearly depicted.

In Step S10, the rectal stool evaluation unit 22 extracts the rectum from the ultrasound image in the region of interest A1 by performing the image analysis on the ultrasound image U acquired in Step S9, to evaluate the rectal stool based on the extracted rectum. In this case, the rectal stool evaluation unit 22 evaluates, for example, whether the rectal stool present inside the extracted rectum is loose stool or hard stool. Further, the rectal stool evaluation unit 22 causes the display unit 16 to display the result of the rectal stool evaluation.

When Step S10 is completed in this way, the operation of the ultrasound diagnostic apparatus 1 ends.

Alternatively, in a case where determination is made in Step S5 that the prostate C is not extracted, the process proceeds to Step S11.

Figure 6:
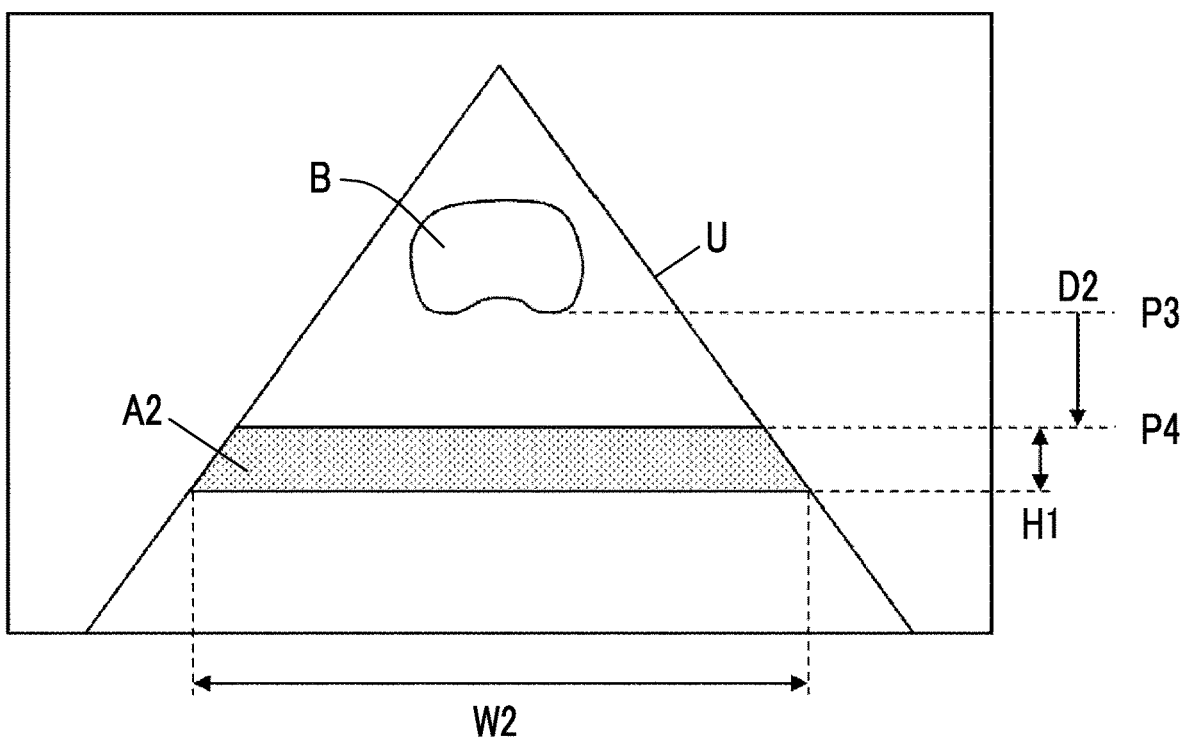
FIG. 6 is a diagram showing a second example of a region of interest according to the first embodiment of the present invention.

In Step S11, for example, as shown in FIG. 6, the region-of-interest setting unit 20 sets a region of interest A2 at a depth position P4 away from the position P3 of the bladder extracted in Step S2 in the depth direction by a predetermined second distance D2. The region of interest A2 is a region in which the rectum is assumed to be present. In FIG. 6, the upper end of the region of interest A2 is positioned at a depth position P4 away from the position P3 of the lower end of the bladder B in the ultrasound image U in the depth direction by a second distance D2. In addition, the region of interest A2 has a trapezoidal shape set over the entire ultrasound image U in the lateral direction, and has a width W2 in the lateral direction. Further, the region of interest A2 has a height H1 in the depth direction. The height H1 of the region of interest A2 is set to have a width of the typical rectum in the depth direction. The second distance D2 between the bladder B and the region of interest A2 is longer than the first distance D1 between the prostate C and the region of interest A1 which is set in Step S6.

In subsequent Step S7, the image quality adjustment unit 21 detects the image quality of the ultrasound image U in the region of interest A2.

In Step S8, the image quality adjustment unit 21 adjusts the transmission/reception conditions of the ultrasonic waves based on the detection result of the image quality in the region of interest A2 in Step S7, and adjusts the image quality of the ultrasound image U to be generated by the image acquisition unit 17 such that the inside of the region of interest A2 is clearly depicted.

In Step S9, the image acquisition unit 17 newly acquires the ultrasound image U. In this ultrasound image U, the image quality adjustment focusing on the region of interest A2 is performed by the image quality adjustment unit 21, so that the rectum which is assumed to be present in the region of interest A2 is clearly depicted.

In Step S10, the rectal stool evaluation unit 22 extracts the rectum from the ultrasound image in the region of interest A2 by performing the image analysis on the ultrasound image U acquired in Step S9, to evaluate the rectal stool based on the extracted rectum. In this case, the rectal stool evaluation unit 22 evaluates, for example, whether the rectal stool present inside the extracted rectum is loose stool or hard stool. Further, the rectal stool evaluation unit 22 causes the display unit 16 to display the result of the rectal stool evaluation.

When Step S10 is completed in this way, the operation of the ultrasound diagnostic apparatus 1 ends.

From the above, with the ultrasound diagnostic apparatus 1 according to the first embodiment of the present invention, the region-of-interest setting unit 20 sets the region of interest A1 at the depth position P2 based on the position P1 of the prostate C of the subject extracted by the prostate extraction unit 19, or the region-of-interest setting unit 20 sets the region of interest A2 at the depth position P4 based on the position P3 of the bladder B extracted by the bladder extraction unit 18, and then the image quality adjustment of the ultrasound image U focusing on the set region of interest A1 or A2 is automatically performed. Therefore, in order to adjust the image quality of the ultrasound image U, the user does not need to manually adjust the transmission/reception conditions of the ultrasonic waves, so that the effort required for the examination can be reduced. In addition, it is usually difficult for the low-skilled user to clearly depict the inside of the region of interest A1 or A2 by adjusting the transmission/reception conditions of the ultrasonic waves, but with the ultrasound diagnostic apparatus 1, the examination can be easily performed regardless of the skill level of the user.

Further, in a case where the prostate C is enlarged, the enlarged prostate C pushes the bladder B up toward the shallow side and the rectum down toward the deep side. In this case, the distance from the lower end of the bladder B to the rectum becomes longer, but the distance from the lower end of the prostate C to the rectum does not change much. Therefore, in a case where the prostate C is depicted, it is preferable to set the region of interest A1 not based on the depth position of the bladder B but based on the position P1 of the prostate C.

In addition, as shown in FIGS. 5 and 6, the region-of-interest setting unit 20 sets the region of interest A1 or A2 over the entire ultrasound image U in the lateral direction, but a setting method of a region of interest is not limited thereto.

Figure 7:
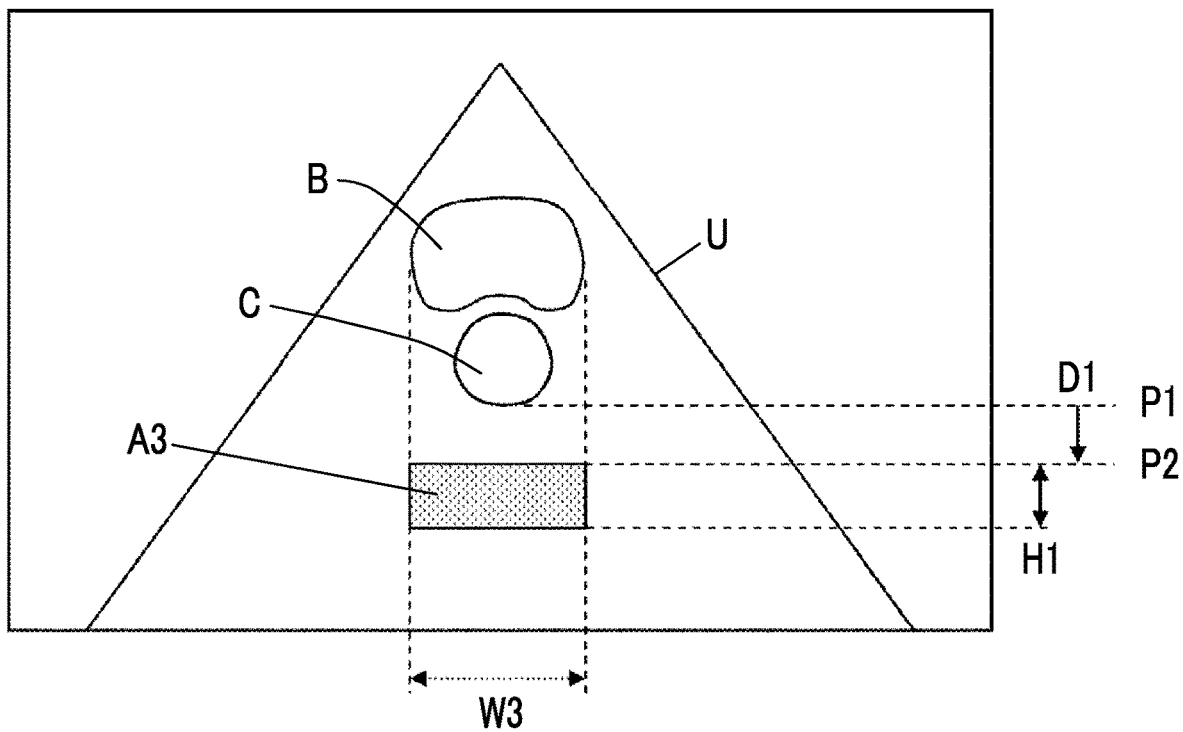
FIG. 7 is a diagram showing a third example of a region of interest according to the first embodiment of the present invention.

For example, in a case where the prostate C of the subject is extracted by the prostate extraction unit 19, as shown in FIG. 7, the region-of-interest setting unit 20 may set a rectangular region of interest A3 having the width W3 which corresponds to the lateral width of the bladder B, at the depth position P2 away from the position P1 of the prostate C in the depth direction by a first distance D1. Further, the region of interest A3 is disposed at the lateral position corresponding to the position of the bladder B, and in the lateral direction of the ultrasound image U, the positions of both ends of the region of interest A3 in the lateral direction match the positions of the corresponding both ends of the bladder B in the lateral direction, respectively. Here, the rectum is usually positioned within the range of the lateral width of the bladder B. Therefore, the region-of-interest setting unit 20 may set the region of interest A3 as a region in which the rectum is assumed to be present even in a case where the lateral width W of the region of interest A3 is set to have the same length as the lateral width of the bladder B.

Further, by setting the lateral width W of the region of interest A3 to have the same length as the lateral width of the bladder B, the region of interest A3 can be set in a narrow region, as compared with the case where the region of interest is set over the entire ultrasound image U in the lateral direction. Therefore, based on the region of interest A3, the image quality of the ultrasound image U can be more easily adjusted in a short time.

Figure 8:
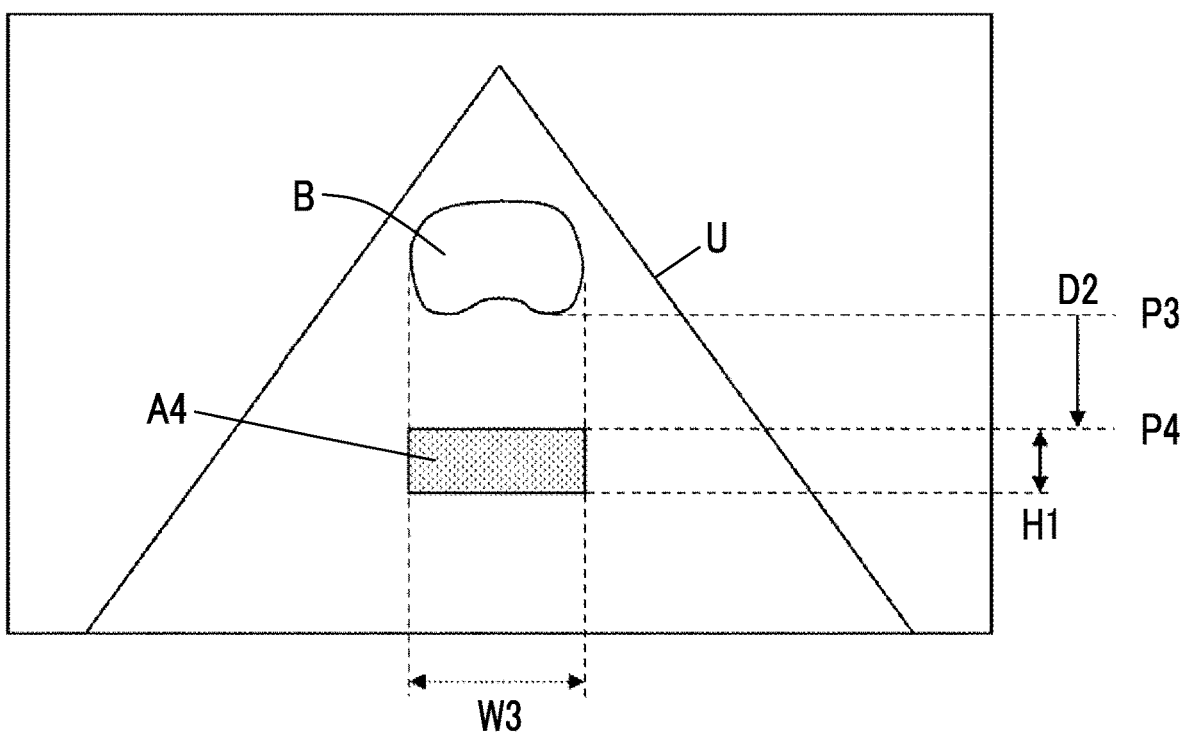
FIG. 8 is a diagram showing a fourth example of a region of interest according to the first embodiment of the present invention.

Alternatively, for example, in a case where the prostate C of the subject is not extracted by the prostate extraction unit 19, as shown in FIG. 8, the region-of-interest setting unit 20 may set a rectangular region of interest A4 having the width W3 which corresponds to the lateral width of the bladder B, at the depth position P4 away from the position P3 of the bladder B by a second distance D2. Further, as in the region of interest A3 shown in FIG. 7, the region of interest A4 is disposed at the lateral position corresponding to the position of the bladder B, and in the lateral direction of the ultrasound image U, the positions of both ends of the region of interest A4 in the lateral direction match the positions of the corresponding both ends of the bladder B in the lateral direction, respectively. Also in this case, in the same manner as in the case of setting the region of interest A3 shown in FIG. 7, the region-of-interest setting unit 20 sets the region of interest A4 as a region in which the rectum is assumed to be present. Therefore, based on the region of interest A4, the image quality of the ultrasound image U can be more easily adjusted in a short time.

Second Embodiment

Figure 9:
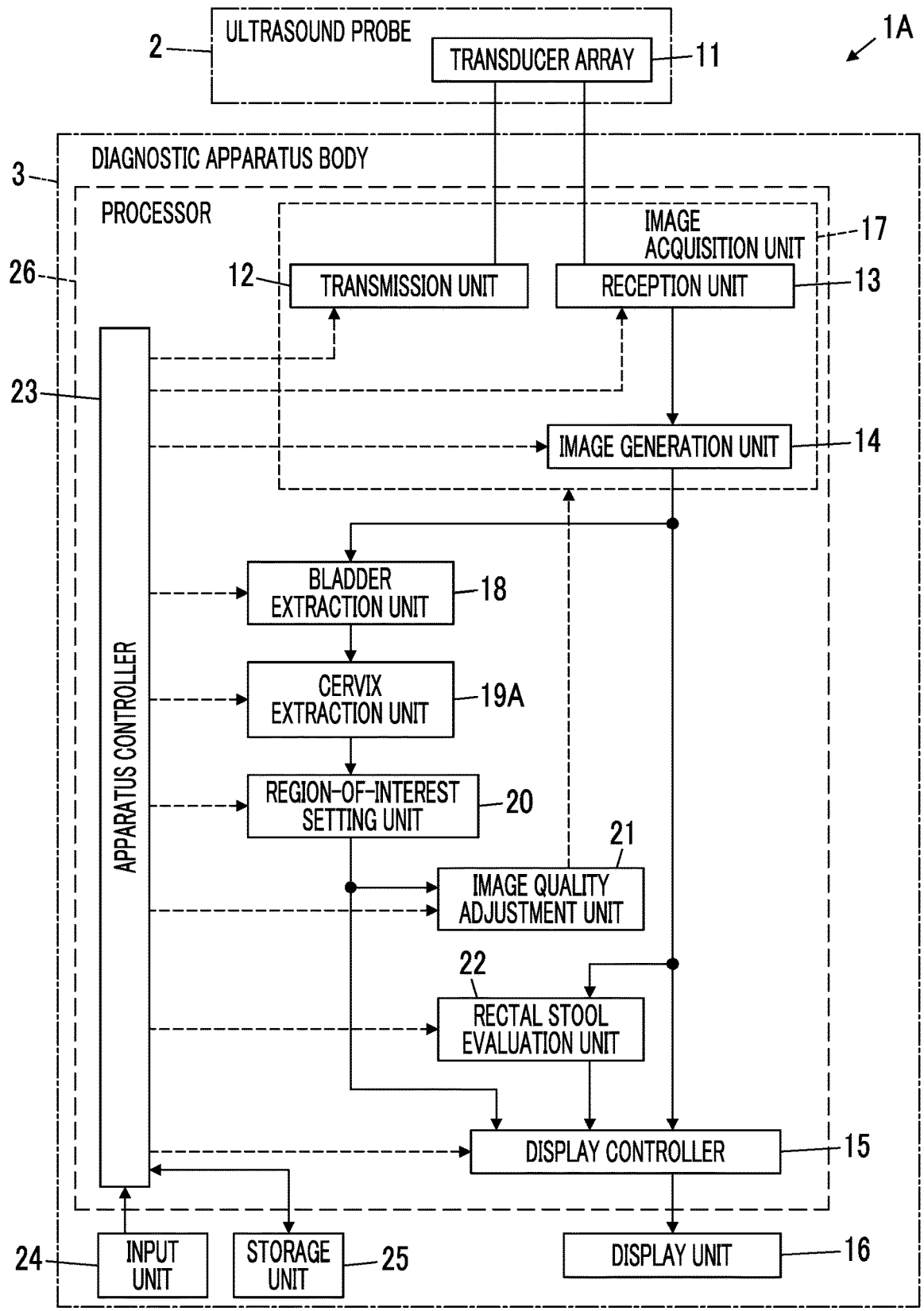
FIG. 9 is a block diagram showing a configuration of an ultrasound diagnostic apparatus according to a second embodiment of the present invention.

The ultrasound diagnostic apparatus 1 according to the first embodiment extracts the prostate C from the ultrasound image U, but may extract a cervix instead of extracting the prostate C. FIG. 9 shows an ultrasound diagnostic apparatus 1A according to a second embodiment. The ultrasound diagnostic apparatus 1A comprises a cervix extraction unit 19A, instead of the prostate extraction unit 19 in the ultrasound diagnostic apparatus 1 according to the first embodiment shown in FIG. 1. The cervix is anatomically present at the same position as the prostate C, and thus the cervix is positioned at a position P1 below the bladder B, as in the position of the prostate C shown in FIG. 5.

Accordingly, with the ultrasound diagnostic apparatus 1A according to the second embodiment of the present invention, in the same manner as the ultrasound diagnostic apparatus 1 according to the first embodiment, the region-of-interest setting unit 20 sets the region of interest A1 at the depth position P2 based on the position P1 of the cervix of the subject extracted by the cervix extraction unit 19A, or the region-of-interest setting unit 20 sets the region of interest A2 at the depth position P4 based on the position P3 of the bladder B extracted by the bladder extraction unit 18, and then the image quality adjustment of the ultrasound image U focusing on the set region of interest A1 or A2 is automatically performed. As a result, as in the ultrasound diagnostic apparatus 1 according to the first embodiment, in the ultrasound diagnostic apparatus 1A, the user does not need to manually adjust the transmission/reception conditions of the ultrasonic waves so as to adjust the image quality of the ultrasound image U, and thus the efforts required for the examination can be reduced. In addition, it is usually difficult for the low-skilled user to clearly depict the inside of the region of interest A1 or A2 by adjusting the transmission/reception conditions of the ultrasonic waves, but with the ultrasound diagnostic apparatus 1, the examination can be easily performed regardless of the skill level of the user.

EXPLANATION OF REFERENCES

1, 1A: ultrasound diagnostic apparatus
2: ultrasound probe
3: diagnostic apparatus body
11: transducer array
12: transmission unit
13: reception unit
14: image generation unit
15: display controller 16: display unit
17: image acquisition unit
18: bladder extraction unit
19: prostate extraction unit
19A: cervix extraction unit
20: region-of-interest setting unit
21: image quality adjustment unit
22: rectal stool evaluation unit
23: apparatus controller
24: input unit
25: storage unit
26: processor
27: amplification unit
28: AD conversion unit
29: beamformer
30: signal processing unit
31: DSC
32: image processing unit
A1, A2, A3, A4: region of interest
B: bladder
C: prostate
D1: first distance
D2: second distance
H1: height
P1, P3: position
P2, P4: depth position
W1, W2: width
U: ultrasound image

What is claimed is:

1. An ultrasound diagnostic apparatus comprising:
an ultrasound probe;
a display that displays an ultrasound image of a subject; and
a processor configured to function as
an image acquisition unit that acquires the ultrasound image of the subject by performing transmission and reception of an ultrasound beam to and from the ultrasound probe in accordance with a predetermined transmission/reception condition,
a bladder extraction unit that extracts a bladder based on the ultrasound image acquired by the image acquisition unit,
a prostate extraction unit that extracts a prostate based on the ultrasound image from which the bladder is extracted by the bladder extraction unit,
a region-of-interest setting unit that sets a region of interest at a depth position in the ultrasound image based on a position of the extracted prostate in a case where the prostate is extracted by the prostate extraction unit and that sets a region of interest at a depth position in the ultrasound image based on a position of the bladder extracted by the bladder extraction unit in a case where the prostate is not extracted by the prostate extraction unit, and
an image quality adjustment unit that adjusts the transmission/reception condition according to the depth position of the region of interest set by the region-of-interest setting unit.

2. The ultrasound diagnostic apparatus according to claim 1,
wherein in a case where the prostate is extracted by the prostate extraction unit, the region-of-interest setting unit sets the region of interest at a position deeper than the position of the extracted prostate by a predetermined first distance.

3. The ultrasound diagnostic apparatus according to claim 2,
wherein the region-of-interest setting unit sets the region of interest having a width corresponding to a width of the bladder at a lateral position corresponding to the position of the bladder extracted by the bladder extraction unit.

4. The ultrasound diagnostic apparatus according to claim 2,
wherein the region-of-interest setting unit sets the region of interest over an entire ultrasound image in a lateral direction at the depth position of the region of interest.

5. The ultrasound diagnostic apparatus according to claim 1,
wherein in a case where the prostate is not extracted by the prostate extraction unit, the region-of-interest setting unit sets the region of interest at a position deeper than the position of the bladder extracted by the bladder extraction unit by a second distance longer than a predetermined first distance.

6. The ultrasound diagnostic apparatus according to claim 5,
wherein the region-of-interest setting unit sets the region of interest having a width corresponding to a width of the bladder at a lateral position corresponding to the position of the bladder extracted by the bladder extraction unit.

7. The ultrasound diagnostic apparatus according to claim 5,
wherein the region-of-interest setting unit sets the region of interest over an entire ultrasound image in a lateral direction at the depth position of the region of interest.

8. The ultrasound diagnostic apparatus according to claim 1,
wherein the image quality adjustment unit adjusts a gain of the ultrasound image according to an image quality of the ultrasound image in the region of interest.

9. The ultrasound diagnostic apparatus according to claim 1,
wherein the image quality adjustment unit adjusts a dynamic range of the ultrasound image according to an image quality of the ultrasound image in the region of interest.

10. The ultrasound diagnostic apparatus according to claim 1,
wherein the processor is further configured to function as
a rectal stool evaluation unit that evaluates rectal stool, based on the ultrasound image acquired by the image acquisition unit in accordance with the transmission/reception condition adjusted by the image quality adjustment unit.

11. An ultrasound diagnostic apparatus comprising:
an ultrasound probe;
a display that displays an ultrasound image of a subject; and
a processor configured to function as
an image acquisition unit that acquires an ultrasound image of a subject by performing transmission and reception of an ultrasound beam to and from the ultrasound probe in accordance with a predetermined transmission/reception condition,
a bladder extraction unit that extracts a bladder based on the ultrasound image acquired by the image acquisition unit,
a cervix extraction unit that extracts a cervix based on the ultrasound image from which the bladder is extracted by the bladder extraction unit,
a region-of-interest setting unit that sets a region of interest at a depth position in the ultrasound image based on a position of the extracted cervix in a case where the cervix is extracted by the cervix extraction unit and that sets a region of interest at a depth position in the ultrasound image based on a position of the bladder extracted by the bladder extraction unit in a case where the cervix is not extracted by the cervix extraction unit; and an image quality adjustment unit that adjusts the transmission/reception condition according to the depth position of the region of interest set by the region-of-interest setting unit.

12. The ultrasound diagnostic apparatus according to claim 11,
wherein in a case where the cervix is extracted by the cervix extraction unit, the region-of-interest setting unit sets the region of interest at a position deeper than the position of the extracted cervix by a predetermined first distance.

13. The ultrasound diagnostic apparatus according to claim 12,
wherein the region-of-interest setting unit sets the region of interest having a width corresponding to a width of the bladder at a lateral position corresponding to the position of the bladder extracted by the bladder extraction unit.

14. The ultrasound diagnostic apparatus according to claim 12,
wherein the region-of-interest setting unit sets the region of interest over an entire ultrasound image in a lateral direction at the depth position of the region of interest.

15. The ultrasound diagnostic apparatus according to claim 11,
wherein in a case where the cervix is not extracted by the cervix extraction unit, the region-of-interest setting unit sets the region of interest at a position deeper than the position of the bladder extracted by the bladder extraction unit by a second distance longer than a predetermined first distance.

16. The ultrasound diagnostic apparatus according to claim 15,
wherein the region-of-interest setting unit sets the region of interest having a width corresponding to a width of the bladder at a lateral position corresponding to the position of the bladder extracted by the bladder extraction unit.

17. The ultrasound diagnostic apparatus according to claim 15,
wherein the region-of-interest setting unit sets the region of interest over an entire ultrasound image in a lateral direction at the depth position of the region of interest.

18. The ultrasound diagnostic apparatus according to claim 11,
wherein the image quality adjustment unit adjusts a gain of the ultrasound image according to an image quality of the ultrasound image in the region of interest.

19. The ultrasound diagnostic apparatus according to claim 11,
wherein the image quality adjustment unit adjusts a dynamic range of the ultrasound image according to an image quality of the ultrasound image in the region of interest.

20. The ultrasound diagnostic apparatus according to claim 11,
wherein the processor is further configured to function as
a rectal stool evaluation unit that evaluates rectal stool, based on the ultrasound image acquired by the image acquisition unit in accordance with the transmission/reception condition adjusted by the image quality adjustment unit.

21. A control method of an ultrasound diagnostic apparatus, comprising:
acquiring an ultrasound image of a subject by performing transmission and reception of an ultrasound beam to and from the ultrasound probe in accordance with a predetermined transmission/reception condition;
displaying the acquired ultrasound image;
extracting a bladder based on the acquired ultrasound image;
extracting a prostate or cervix based on the ultrasound image from which the bladder is extracted;
setting a region of interest at a depth position in the ultrasound image based on a position of the extracted prostate or cervix in a case where the prostate or cervix is extracted and setting a region of interest at a depth position in the ultrasound image based on a position of the extracted bladder in a case where the prostate or cervix is not extracted; and
adjusting the transmission/reception condition according to the depth position of the set region of interest.

* * * * *